(12) United States Patent
Kogure et al.

(10) Patent No.: US 7,925,520 B2
(45) Date of Patent: Apr. 12, 2011

(54) METHODS OF PREDICTING DOSE OF DRUG AND PROGRAM FOR PREDICTING DOSE OF DRUG

(75) Inventors: Kentaro Kogure, Sapporo (JP); Kaoru Kigasawa, Sapporo (JP); Naoki Nakamura, Sapporo (JP)

(73) Assignee: TTI ellebeau, Inc., Tokyo (JP)

( * ) Notice: Subject to any disclaimer, the term of this patent is extended or adjusted under 35 U.S.C. 154(b) by 397 days.

(21) Appl. No.: 12/015,449

(22) Filed: Jan. 16, 2008

(65) Prior Publication Data

US 2008/0208106 A1    Aug. 28, 2008

Related U.S. Application Data

(60) Provisional application No. 60/886,210, filed on Jan. 23, 2007.

(30) Foreign Application Priority Data

Jan. 16, 2007    (JP) ................................ 2007-007328

(51) Int. Cl.
    *A61M 31/00*     (2006.01)
    *G06Q 10/00*     (2006.01)

(52) U.S. Cl. .......................................... 705/2; 604/501

(58) Field of Classification Search .............. 604/890.1, 604/20, 21, 501; 705/2
See application file for complete search history.

(56) References Cited

U.S. PATENT DOCUMENTS

| | | | |
|---|---|---|---|
| 5,291,887 A | 3/1994 | Stanley et al. | 128/637 |
| 5,582,586 A | 12/1996 | Tachibana et al. | 604/20 |
| 6,032,073 A * | 2/2000 | Effenhauser | 604/20 |
| 6,391,015 B1 | 5/2002 | Millot | 604/503 |
| 6,394,994 B1 | 5/2002 | Vilambi et al. | 604/501 |
| 6,468,657 B1 * | 10/2002 | Hou et al. | 428/403 |
| 6,692,456 B1 | 2/2004 | Eppstein et al. | 604/22 |
| 6,928,318 B2 | 8/2005 | Simon | 604/20 |
| 6,939,311 B2 | 9/2005 | Geiger | 600/573 |
| 7,018,345 B2 | 3/2006 | Mori et al. | 600/573 |

(Continued)

FOREIGN PATENT DOCUMENTS

EP     0 931 564 A1     7/1999

(Continued)

OTHER PUBLICATIONS

Hirvonen, J., et al., "Experimental Verification of the Mechanistic Model for Transdermal Transport Including Iontophoresis," J. Controlled Release, 56:169-174, 1998.

(Continued)

*Primary Examiner* — Kevin C Sirmons
*Assistant Examiner* — Bradley J Osinski
(74) *Attorney, Agent, or Firm* — Seed IP Law PLLC

(57) ABSTRACT

A migration M of a drug ion in a membrane type iontophoresis device for administering the drug ion through a first ion exchange membrane is predicted on the basis of a migration C of the drug ion from the first ion exchange membrane to the outside of the device in the case where a voltage is applied to an electrode by using the device under such a condition that the first ion exchange membrane is not brought into contact with the skin of a living organism and a migration R of the drug ion to a liposome caused by mixing a liposome solution having a predetermined concentration and a drug solution containing a predetermined concentration of the drug ion.

14 Claims, 8 Drawing Sheets

U.S. PATENT DOCUMENTS

| | | |
|---|---|---|
| 2002/0182485 A1 | 12/2002 | Anderson et al. ............ 429/105 |
| 2003/0185023 A1 | 10/2003 | Hause, Jr. ...................... 363/31 |
| 2004/0087671 A1 | 5/2004 | Tamada et al. ................. 516/99 |
| 2004/0248320 A1 | 12/2004 | Santini, Jr. et al. ........... 436/174 |
| 2005/0267440 A1 | 12/2005 | Herman et al. ............... 604/501 |
| 2006/0024358 A1 | 2/2006 | Santini, Jr. et al. ........... 424/448 |
| 2006/0024359 A1 | 2/2006 | Walker et al. |
| 2006/0094946 A1 | 5/2006 | Kellogg et al. ............... 600/347 |
| 2006/0095001 A1 | 5/2006 | Matsumura et al. ............ 604/20 |
| 2006/0116628 A1 | 6/2006 | Matsumura et al. ............ 604/20 |
| 2006/0129085 A1 | 6/2006 | Tanioka et al. ................. 604/20 |
| 2006/0135906 A1 | 6/2006 | Matsumura et al. ............ 604/20 |
| 2006/0173401 A1 | 8/2006 | Tanioka et al. ................. 604/20 |
| 2006/0217654 A1 | 9/2006 | Matsumura et al. ............ 604/20 |
| 2006/0235351 A1 | 10/2006 | Matsumura et al. ............ 604/20 |
| 2006/0276742 A1 | 12/2006 | Matsumura et al. ............ 604/20 |
| 2006/0286102 A1 | 12/2006 | Jin et al. |
| 2008/0058756 A1 | 3/2008 | Smith ........................... 604/501 |

FOREIGN PATENT DOCUMENTS

| | | |
|---|---|---|
| JP | 06-070987 | 3/1994 |
| JP | 2001-120670 | 5/2001 |
| JP | 2004-024699 | 1/2004 |
| WO | 2006/055729 | 5/2006 |
| WO | 2007/010900 | 1/2007 |
| WO | 2008/027218 | 3/2008 |

OTHER PUBLICATIONS

Kramer. S., "Absorption Prediction from Physicochemical Paratmeters," PSTT, 2(9):373-380, 1999.

Asher, S., et al., "Photonic Crystal Carbohydrate Sensors: Low Ionic Strength Sugar Sensing," *J. Am. Chem. Soc.*, 125(11), 3322-3329, 2003.

JCAAI.org, "Diagnostic Tests of Cell Mediated Immune Reactions (Delayed Hypersensitivity)," *Ann Allergy*, 75:543-625, 1995. URL—http://www.jcaai.org//pp/adt_3-02.asp, retrieved Aug. 23, 2007, 2 pages.

Merclin, N., "Electrochemical Methods for Drug Characterisation and Transdermal Delivery," *Uppsala universitet, doktorsavhandling*, 2003.

\* cited by examiner

METHODS OF PREDICTING DOSE OF DRUG AND PROGRAM FOR PREDICTING DOSE OF DRUG

CROSS-REFERENCES TO RELATED APPLICATIONS

This application claims benefit under 35 U.S.C. §119(e) of U.S. Provisional Application No. 60/886,210 filed Jan. 23, 2007 and 35 U.S.C. 119 of Japanese Application No. 2007-007328 filed Jan. 16, 2007, the entire contents of which are incorporated herein by reference.

BACKGROUND

1. Technical Field

This disclosure generally relates to the field of transdermal administration of active ingredients by iontophoresis and, more particularly, to methods of predicting an amount, a rate, a dose, and/or an efficiency associated with the iontophoretic administration of drug to a living organism.

2. Description of the Related Art

Iontophoresis employs an electromotive force and/or current to transfer an active ingredient (e.g., a charged substance, an ionized compound, an ionic drug, a therapeutic, a bioactive-agent, and the like), to a biological interface (e.g., skin, mucus membrane, and the like), by applying an electrical potential to an electrode proximate an iontophoretic chamber comprising a similarly charged active ingredient and/or its vehicle. For example, a positively charged ion is transferred into the skin at an anode side of an electric system of an iontophoresis device. In contrast, a negatively charged ion is transferred into the skin at a cathode side of the electric system of the iontophoresis device.

Although skin is one of the most extensive and readily accessible organs, it has historically been difficult to deliver certain active agents transdermally. Often a drug is administered to a living body mainly through the corneum of the skin. The corneum, however, is a lipid-soluble high-density layer that makes the transdermal administration of high water-soluble substances and polymers such as peptides, nucleic acids, and the like difficult.

Generally it is difficult to iontophoretically administer an effective dose of a drug without damaging the skin of a living organism. It is also generally difficult to iontophoretically administer an effective dose of a drug within an acceptable time period. Consequently, iontophoresis is clinically used to administer only a limited number of drug types.

Attempts have been made to find correlations between structure, or other characteristic of a drug, and the dose, or delivery rate associated with the iontophoretic administration of the drug to a living organism. Often, however, determining such correlations requires in vivo testing. Accordingly, a need exist for determining, for example, a dose or deliver rate associated with the iontophoretic administration of the drug without the use of in vivo testing.

The present disclosure is directed to overcoming one or more of the shortcomings set forth above, and/or providing further related advantages.

BRIEF SUMMARY

In one aspect, the present disclosure is directed to method of determining an amount of drug deliverable to a biological subject by an iontophoretic delivery device having a drug holding portion for holding a drug solution including drug ions of a first polarity, an electrode coupled to the drug holding portion and operable to apply an electrical potential of the first polarity to a drug solution held in the drug solution holding portion, and a first ion exchange membrane (having an exchange group of the first polarity) in contact with a front surface side of the drug solution holding portion.

The method includes determining a first drug migration parameter indicative of the migration of an amount of drug ions from the first ion exchange membrane to an outermost front surface side of the iontophoretic delivery device. The method further includes determining a second drug migration parameter indicative of the migration of an amount of the drug ions migrated from a volume of a drug ion solution to a plurality of liposome in a volume of a liposome suspension after contacting the volume of the drug ion solution to the volume of the liposome suspension. In some embodiments, the method may further include determining at least one of an iontophoretic drug ion delivery amount, iontophoretic drug ion delivery rate, an efficiency, and a dose based on the determined first drug migration parameter and the determining second drug migration parameter.

In another aspect, the present disclosure is directed to a method of predicting a migration M of a drug ion having a first polarity to an inside of a skin of a living organism via iontophoresis using an iontophoresis device having a drug solution holding portion for holding a drug solution containing the drug ion, a working side electrode for applying a voltage having the first polarity to the drug solution of the drug solution holding portion, and a first ion exchange membrane having the first polarity and placed in contact with the drug solution of the drug solution holding portion on a front surface side of the drug solution holding portion.

The method includes determining a migration C of the drug ion from the first ion exchange membrane to an outside of the iontophoresis device in a case where a voltage is applied to the working side electrode in the device under such a condition that the first ion exchange membrane is not brought into contact with the skin of the living organism. The method may further include determining a migration R of the drug ion to a liposome in a case where a liposome solution having a predetermined concentration and the drug solution containing a predetermined concentration of the drug ion are mixed. The method may further include deriving a migration M of the drug ion to the inside of the skin of the living organism based on the determined migration C and migration R.

In another aspect, the present disclosure is directed to at least one computer readable storage medium comprising instructions that, when executed on a computer, execute a method for determining an amount of drug deliverable to a biological subject by an iontophoretic delivery device having a drug holding portion for holding a drug solution including drug ions of a first polarity, an electrode coupled to the drug holding portion and operable to apply an electrical potential of the first polarity to a drug solution held in the drug solution holding portion, and a first ion exchange membrane, having an exchange group of the first polarity, in contact with a front surface side of the drug solution holding portion.

The method includes determining a first drug migration value indicative of the migration of an amount of drug ions from the first ion exchange membrane to an outermost surface of the iontophoretic delivery device. The method further includes determining a second drug migration value indicative of the migration of an amount of the drug ions migrated from a volume of a drug ion solution to a plurality of liposome in a volume of a liposome suspension after contacting the volume of the drug ion solution to the volume of the liposome suspension. The method further includes determining at least one of an iontophoretic drug ion delivery amount, iontophoretic drug ion delivery rate, an efficiency, and a dose based on the determined first drug migration value and the determining second drug migration value.

In another aspect, the present disclosure is directed to a method of predicting the dose of a drug ion in a membrane type iontophoresis device, that is, an iontophoresis device that administers the drug ion through an ion exchange membrane having the same polarity as that of the drug ion, and a program for predicting the dose of the drug ion.

In another aspect, the present disclosure is directed to methods for reducing the necessity for an animal test upon investigation on the application of a membrane type iontophoresis device to a novel drug to alleviate or dissolve cost-related and ethical problems involved in the execution of a large number of animal tests.

In another aspect, the present disclosure is directed to methods for predicting an amount, rate, and/or the efficiency associated with iontophoretic administration of drugs that have undergone ion dissociation and that are administer through an ion exchange membrane having the same polarity as that of the drug ion, and to the inside of the skin of a living organism.

In yet another aspect, the present disclosure is directed to a method of predicting a migration M of a drug ion having first polarity to an inside of a skin of a living organism in an iontophoresis device. In some embodiments the iontophoresis device includes a drug solution holding portion for holding a drug solution containing the drug ion, a working side electrode for applying a voltage having the first polarity to the drug solution of the drug solution holding portion, and a first ion exchange membrane having the first polarity and placed in contact with the drug solution of the drug solution holding portion on a front surface side of the drug solution holding portion in a case where a voltage is applied to the working side electrode in a state where the first ion exchange membrane is brought into contact with the skin of the living organism.

In some embodiments, the method includes deriving the migration M of the drug ion to the inside of the skin of the living organism in the iontophoresis device on the basis of: a migration C of the drug ion from the first ion exchange membrane to an outside of the iontophoresis device in a case where a voltage is applied to the working side electrode in the device under such a condition that the first ion exchange membrane is not brought into contact with the skin of the living organism; and a migration R of the drug ion to a liposome in a case where a liposome solution having a predetermined concentration and the drug solution containing a predetermined concentration of the drug ion are mixed. In yet another aspect, the present disclosure is directed to a program characterized by including a causing processing unit to execute the process of deriving the migration M of the drug ion to the inside of the skin of the living organism in the iontophoresis device on the basis of a migration C and a migration.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements, as drawn, are not intended to convey any information regarding the actual shape of the particular elements, and have been solely selected for ease of recognition in the drawings.

DETAILED DESCRIPTION

Figure 1A:
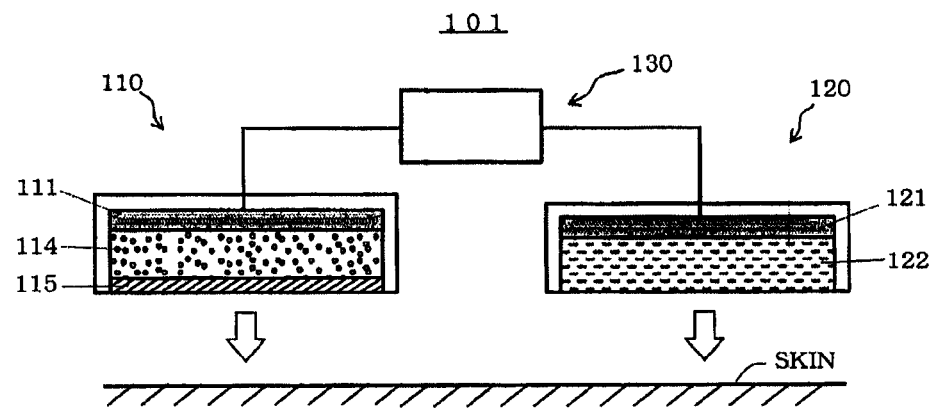
FIG. 1A is a schematic diagram of a membrane type iontophoresis device.

In the following description, certain specific details are included to provide a thorough understanding of various disclosed embodiments. One skilled in the relevant art, however, will recognize that embodiments may be practiced without one or more of these specific details, or with other methods, components, materials, etc. In other instances, well-known structures associated with electrically powered devices including but not limited to voltage and/or current regulators have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment," or "an embodiment," or "in another embodiment," or "in some embodiments" means that a particular referent feature, structure, or characteristic described in connection with the embodiment is included in at least one embodiment. Thus, the appearance of the phrases "in one embodiment," or "in an embodiment," or "in another embodiment," or "in some embodiments" in various places throughout this specification are not necessarily all referring to the same embodiment.

Furthermore, the particular features, structures, or characteristics may be combined in any suitable manner in one or more embodiments.

It should be noted that, as used in this specification and the appended claims, the singular forms "a," "an," and "the" include plural referents unless the content clearly dictates otherwise. Thus, for example, reference to an iontophoretic delivery device, including a "drug" includes a single type of drugs, or two or more types of drugs. It should also be noted that the term "or" is generally employed in its sense including "and/or" unless the content clearly dictates otherwise.

Researchers have reported that the dose of a drug ion delivered iontophoretically to a living organism increases as the molecular weight decreases for drug ions having a moderate hydrophobicity. But such observations are not valid with respect to a membrane type iontophoresis device, and there are no known findings concerning what physical properties of the drug affect the dose of the drug ion in the membrane type iontophoresis device.

The term "migration M" generally refers to the amount of the drug ion that migrates to the living organism in response to energization (e.g., applying a potential, supplying a current, and the like) in the membrane type iontophoresis device in a state where the skin of the living organism is brought into contact with a first ion exchange membrane.

The term "migration C" generally refers to the amount of the drug ion that migrates from the first ion exchange membrane to the outside of a system by in response to energization in the membrane type iontophoresis device in a state where the first ion exchange membrane is brought into contact with, for example, an electrolyte solution outside the system that does not include iontophoretically delivering the drug ion through the skin of the living organism.

The term "migration R" generally refers to the migration of the drug ion to a liposome in the case where a liposome solution having a predetermined concentration and a drug solution containing a predetermined concentration of the drug ion are mixed.

It should be noted that the "migration" of the drug ion to the inside of the skin of the living organism is particularly represented as "administration" in some embodiments. In addition, the "migration rate" of the drug ion is a value obtained by, for example, representing the "migration" normalized with respect to a unit time, the "migration efficiency" of the drug ion is obtained by representing the "migration" as a value per unit energization current or as a ratio relative to the migration of a specific ion kind except the drug ion, and the terms "migration," "migration rate," and "migration efficiency" are used interchangeably.

The term "drug" generally refers to a substance which may be or may not be prepared, which has a certain drug effect or pharmacological action, and which is applicable to an organism for purposes including: the therapy, recovery, or prevention of a disease; the promotion or maintenance of the health; the diagnosis of the medical or health condition; cosmetic procedures, or the promotion or maintenance of beauty.

The term "drug ion" generally refers to an ion which is produced by the dissociation of a drug to ions and which plays a role in a drug effect or a pharmacological action.

The term "drug counter ion" generally refers to an ion which is produced by the dissociation of a drug to ions and which has a polarity opposite to a drug ion.

The term "drug solution" generally refers to a fluid substance containing the drug ion. The term "drug solution" generally includes not only liquid states such as a solution prepared by dissolving a drug into a solvent and a stock solution when a drug is in a liquid state, but also various states such as a drug suspended or emulsified into a solvent or the like and the drug in the form of an ointment or a paste as long as at least part of the drug dissociates to drug ions.

The term "skin" generally refers to the surface of an organism to which a drug ion can be administered by iontophoresis, and includes a mucosa in an oral cavity. The term "organism" generally refers to a human being or an animal.

The term "biological counter ion" generally refers to an ion which is present on the skin of an organism or in the organism and which has a polarity opposite to a drug ion.

The term "front surface side" generally refers to a side close to the skin of an organism on a current path flowing in the device upon administration of a drug ion.

The term "first polarity" generally refers to plus or minus electrical polarity, and the term "second polarity" generally refers to the electrical polarity (minus or plus) opposite to the first polarity.

Known examples of an ion exchange membrane include various ion exchange membranes such as: an ion exchange resin formed into a membrane shape; a heterogeneous ion exchange membrane obtained by dispersing an ion exchange resin into a binder polymer and by forming the resultant into a membrane through, for example, molding under heat; and a homogeneous ion exchange membrane obtained by impregnating and filling a base material such as a cloth, a network, or a porous film with a solution prepared by dissolving, into a solvent, a composition composed of a monomer, crosslinkable monomer, polymerization initiator, or the like in which an ion exchange group can be introduced or a resin having a functional group in which an ion exchange group can be introduced, by subjecting the resultant to polymerization or solvent removal, and by subjecting the resultant to a treatment for introducing an ion exchange membrane. In some embodiments, the ion exchange membrane may comprise any suitable ion exchange membranes without particular limitation.

The term "ion exchange membrane having the first polarity" generally refers to an ion exchange membrane having a function of substantially blocking the passage of an ion having the second polarity while substantially allowing the passage of an ion having the first polarity (that is, an ion exchange membrane through which the ion having the first polarity passes more easily than the ion having the second polarity). When the first polarity is positive, the "ion exchange membrane having the first polarity" is a cation exchange membrane, and when the first polarity is negative, the "ion exchange membrane having the first polarity" is an anion exchange membrane.

Similarly, the term "ion exchange membrane having the second polarity" generally refers to an ion exchange membrane having a function of substantially blocking the passage of an ion having the second polarity while substantially allowing the passage of an ion having the second polarity (that is, an ion exchange membrane through which the ion having the second polarity passes more easily than the ion having the first polarity). When the second polarity is positive, the "ion exchange membrane having the second polarity" is a cation exchange membrane, and when the second polarity is negative, the "ion exchange membrane having the second polarity" is an anion exchange membrane.

Specific examples of the cation exchange membrane include an ion exchange membrane into which a cation exchange group is introduced, such as a NEOSEPTA (CM-1, CM-2, CMX, CMS, or CMB) manufactured by Tokuyama Co., Ltd. Specific examples of the anion exchange membrane include an ion exchange membrane into which an anion exchange group is introduced, such as a NEOSEPTA (AM-1, AM-3, AMX, AHA, ACH, or ACS) manufactured by Tokuyama Co., Ltd.

Examples of exchange membranes include ion exchange membranes of a type in which a porous film is filled with an ion exchange resin can be particularly preferably used. Specifically, an ion exchange membrane obtained by filling a porous film with an ion exchange resin at a filling ratio of preferably 5 to 95 mass %, more preferably 10 to 90 mass %, or particularly preferably 20 to 60 mass % can be used, the porous film having formed thereon a large number of small pores having a mean pore size of preferably 0.005 to 5.0 µm, more preferably 0.01 to 2.0 µm, or most preferably 0.02 to 0.2 µm (a mean flow pore size measured according to the bubble point method (JIS K3832-1690)) at a porosity of preferably 20 to 95%, more preferably 30 to 90%, or most preferably 30 to 60% and having a thickness of preferably 5 to 140 µm, more preferably 10 to 120 µm, or most preferably 15 to 55 µm.

The expression "substantially blocking the passage of an ion" as used to describe an ion selective membrane or an ion exchange membrane does not necessarily mean that no ion is allowed to pass, and includes, for example, the case where a function requested of the ion selective membrane or the ion exchange membrane is sufficiently exerted because a rate at or an amount in which a specific ion passes through each of the membranes is sufficiently small as compared to that of another specific ion. Similarly, the expression "substantially allowing the passage of an ion" to be described for an ion selective membrane or an ion exchange membrane does not mean that no restriction is imposed on the passage of the ion, and includes, for example, the case where a rate at or an amount in which the ion passes through each of the ion selective membrane and the ion exchange membrane is secured to such an extent that a function requested of each of the membranes is sufficiently exerted even when the passage of the ion is restricted to some extent.

There are known iontophoretic devices capable of administering a various kinds of drugs, within a short period of time, using a weak current. See e.g., JP 4-297277 A. For example, FIG. 1A show an iontophoresis device 101 including a working side assembly 110 having an electrode 111, a drug solution holding portion 114 for holding a drug solution containing a drug ion having positive or negative polarity (first polarity), and an ion exchange membrane 115 having the first polarity; a non-working side assembly 120 having an electrode 121 and an electrolyte solution holding portion 122 for holding an electrolyte solution in contact with the electrode 121; and a power supply 130 whose both terminals are connected to the electrodes 111 and 121. A voltage having a first polarity is applied to the electrode 111 and a voltage having a second polarity is applied to the electrode 121 in a state where the ion exchange membrane 115 and the electrolyte solution holding portion 122 are brought into contact with the skin of a living organism, whereby the drug ion of the drug solution holding portion 114 migrates to the side of the living organism through the ion exchange membrane 115.

In the iontophoresis device 101, the ion exchange membrane 115 substantially blocks the migration of a biological counter ion from the skin of the living organism to the drug solution holding portion 114 while substantially allowing the migration of the drug ion to the side of the living organism, so the quantity of a current to be consumed by the movement of the biological counter ion is reduced. As a result, the rate at which the drug ion is administered can be increased.

It should be noted that an iontophoresis device that administers a drug ion to a living organism through an ion exchange membrane having the same polarity as that of the drug ion like the iontophoresis device 101 is hereinafter referred to as "membrane type iontophoresis device."

Figure 1B:
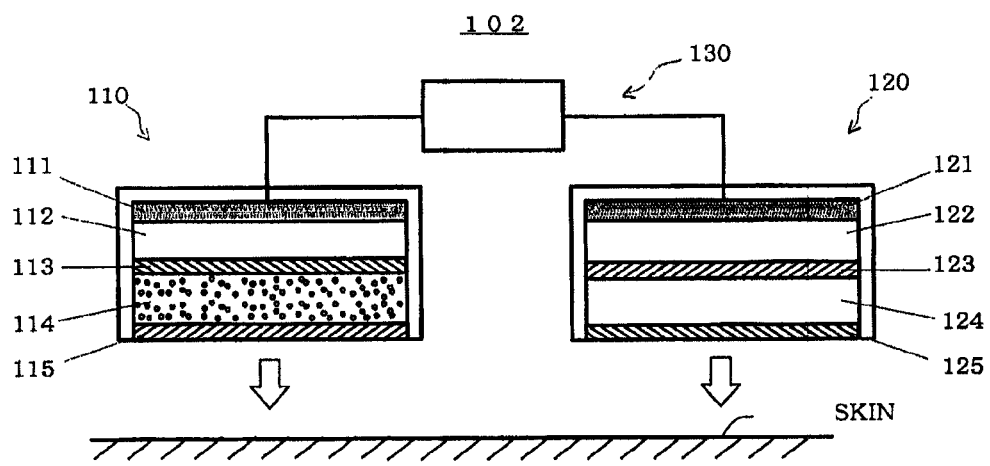
FIG. 1B is a schematic diagram of a membrane type iontophoresis device.

FIG. 1B shows another membrane type iontophoresis device 102. See e.g., JP 2000-229128 A. The membrane type iontophoresis device 102 includes the following components in addition to the respective components provided for the iontophoresis device 101. The membrane type iontophoresis device 102 includes the working side assembly 110 and further includes an electrolyte solution holding portion 112 for holding an electrolyte solution in contact with the electrode 111 and an ion exchange membrane 113 having the second polarity and placed on the front surface side of the electrolyte solution holding portion 112. The non-working side assembly 120 further includes an ion exchange membrane 123 having the first polarity and placed on the front surface side of the electrolyte solution holding portion 122, an electrolyte solution holding portion 124 placed on the front surface side of the ion exchange membrane 123, and an ion exchange membrane 125 having the second polarity and placed on the front surface side of the electrolyte solution holding portion 124.

The membrane type iontophoresis device 102 is capable of achieving not only effects similar to those described above for the membrane type iontophoresis device 101, but also the following additional effects:

(1) the action of the ion exchange membrane 113 having the second polarity substantially blocks the migration of the drug ion to the electrolyte solution holding portion 112, whereby the decomposition of a drug near the electrode 111 upon energization (e.g., application of a potential, supplying of a current, and the like) can be prevented;

(2) even when hazardous ions (such as a hydrogen ion, a hydroxyl ion, and a hypochlorite ion) are generated near the electrode 111 or 121 owing to an electrode reaction, the actions of the ion exchange membrane 113 having the second polarity and the ion exchange membrane 123 having the first polarity can prevent or reduce those hazardous ions from migrating to the side of the skin of the living organism; and (3) the action of the ion exchange membrane 125 having the second polarity allows an ion balance at a skin interface during the administration of the drug ion to be favorably maintained, whereby damage to the skin due to energization for the administration of the drug ion can be additionally reduced.

There are not many examples of membrane type iontophoresis in commercial use, and there are no known reports on what physical property of a drug ion affects the dose of the drug ion to a living organism in the membrane type iontophoresis device. Further, it has been determined that a significant correlation between the hydrophobicity or the like of a drug and the dose of the drug is not present in the membrane type iontophoresis device, and methods of predicting the dose of the drug in conventional iontophoresis are not generally applicable to the membrane type iontophoresis device.

The present disclosure includes the evaluation, through the accumulation of a large number of experiments, of various miscellaneous structural characteristics, and physical and chemical characteristics possessed by a drug or a drug ion for its influence on the dose of the drug ion in a membrane type iontophoresis device. During the foregoing process, it was found that the dose of the drug ion in the membrane type iontophoresis device can be accurately predicted on the basis of a small number of factors whose data can be relatively easily collected.

To be more specific, when C represents the migration of the drug ion migrating from a first ion exchange membrane to the outside of the membrane type iontophoresis device in the case where energization ion (e.g., applying a potential, supplying a current, and the like) is performed in the device under such a condition that the first ion exchange membrane is not brought into contact with the skin of a living organism, R represents the migration of the drug ion to a liposome in the case where a liposome solution having a predetermined concentration and a drug solution containing a predetermined concentration of the drug ion are mixed, and $A_1$ and $A_2$ each represent constants.

In some embodiments, a migration M of the drug ion to a living organism via iontophoretic delivery using, for example, a membrane type iontophoresis device can be predicted from the following Equation (1):

$$\mathrm{Log}(M/C) = A_1 \mathrm{Log} R + A_2 \qquad (\text{Eq. 1}).$$

Data for deriving the constants $A_1$ and $A_2$ in Equation 1 can be collected by unifying, for example, the following conditions (because the constants $A_1$ and $A_2$ vary depending on those conditions).

Is some embodiments, constants $A_1$ and $A_2$ may be determined based on the specification of the first ion exchange membrane (such as the kind of an ion exchange group, the thickness, effective area, and composition of the membrane, and a production method for the membrane), administration conditions (such as an energization condition, the kind of a body to be administered, and a site to which the body is administered), and the construction of the device (such as, for example, whether the iontophoresis device includes an additional element such as a second ion exchange membrane).

Some of the disclosed embodiments are generally applicable to a membrane type iontophoresis device that administers a drug ion through an ion exchange membrane having the same polarity as that of the drug ion (first ion exchange membrane), and is similarly applicable to any one of the following iontophoresis devices each having additional components:

(1) an iontophoresis device in which a working side assembly for carrying the drug ion to be administered to a living organism has an ion exchange membrane having polarity opposite to that of the drug ion (second ion exchange membrane) between a working side electrode and a drug solution containing the drug ion;

(2) an iontophoresis device in which the working side assembly has an electrolyte solution between the working side electrode and the second ion exchange membrane in addition to the constitution described in the above item (1);

(3) an iontophoresis device in which a non-working side assembly to be used as a counter electrode for the working side assembly has an ion exchange membrane having polarity opposite to that of the drug ion (third ion exchange membrane) and an electrolyte solution placed between a non-working side electrode and the third ion exchange membrane (non-working side first electrolyte solution); and (4) an iontophoresis device in which the non-working side assembly has an ion exchange membrane having the same polarity as that of the drug ion (fourth ion exchange membrane) between the non-working side electrode and the non-working side first electrolyte solution, and further, an electrolyte solution between the non-working side electrode and the fourth ion exchange membrane (non-working side second electrolyte solution) in addition to the constitution described in the above item (3).

Figure 1C:
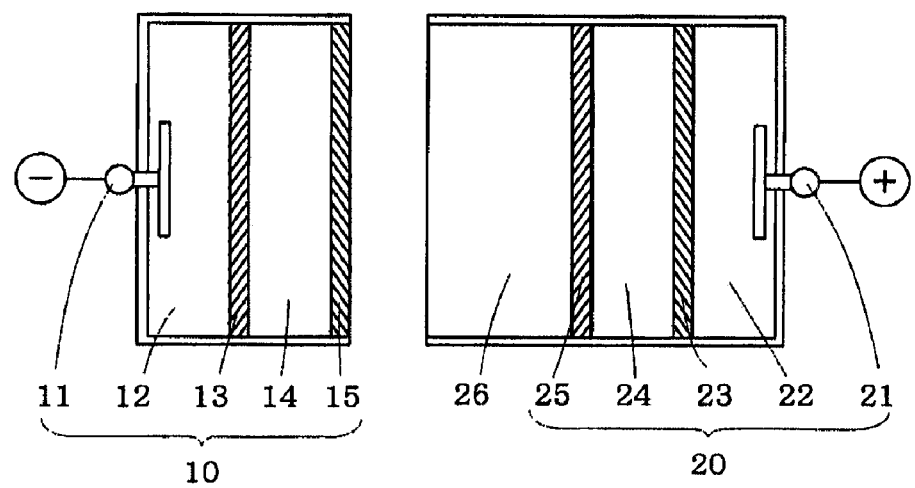
FIG. 1C is a schematic diagram of an in vitro experimental setup including a membrane type iontophoresis device used to obtain data for predicting the migration of drug ions according to one illustrative embodiment.

FIG. 1C shows a membrane type iontophoresis device 1 used in: the collection of data for deriving a function to be used in a method of predicting the migration M of a drug ion according to some embodiments.

As shown in the FIG. 1C, the iontophoresis device 1 may be the same or different than the membrane type iontophoresis device 102. In some embodiments, a working side assembly 10 of the device 1 may include a working side electrode (negative electrode) 11; an electrolyte solution holding portion 12 for holding a physiological salt solution; a cation exchange membrane 13 on the front surface side of the electrolyte solution holding portion; a drug solution holding portion 14 for holding a drug solution on the front surface side of the cation exchange membrane 13; and an anion exchange membrane 15 on the front surface side of the drug solution holding portion.

In some embodiments, a non-working side assembly 20 of the device 1 may include a non-working side electrode (positive electrode) 21; an electrolyte solution holding portion 22 for holding a physiological salt solution; an anion exchange membrane 23 on the front surface side of the electrolyte solution holding portion 22; an electrolyte solution holding portion 24 for holding a physiological salt solution on the front surface side of the anion exchange membrane 23; and a cation exchange membrane 25 on the front surface side of the electrolyte solution holding portion 24. It should be noted that an ion exchange membrane CLE 04-2 manufactured by Tokuyama Co., Ltd. was used as each of the ion exchange membrane 13 and the ion exchange membrane 25, and an ion exchange membrane ALE 04-2 manufactured by Tokuyama Co., Ltd. was used as each of the ion exchange membrane 15 and the ion exchange membrane 23.

In addition, an electrolyte solution holding portion 26 capable of holding a sufficient amount of a physiological salt solution is attached to the front surface side of the cation exchange membrane 25 of the non-working side assembly 20.

The following measurements were performed with the iontophoresis device 1. It should be noted that eight kinds of anionic drugs containing non-steroidal anti-inflammatory agents represented by the following structural formulae (a) to (h) (Diclofenac (DFS), Felbinac (FBN), Ketoprofen (KPF), Indomethacin (IDM), Salicylic acid (SA), Etodolac (EDC), 3-Indoleacetic acid (IAA), and Naproxen (NPX)) were used as samples.

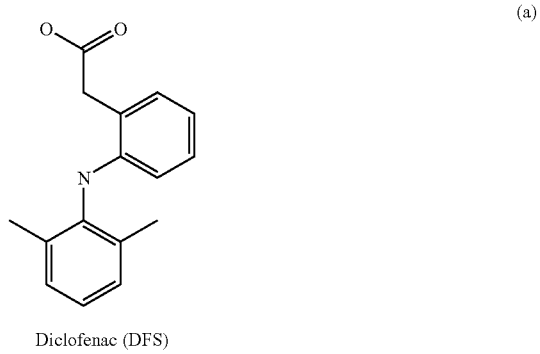

Diclofenac (DFS)

(a)

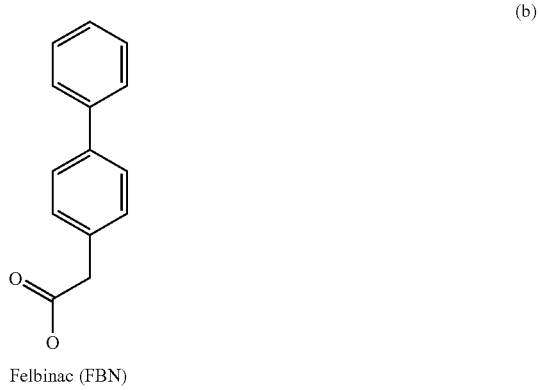

Felbinac (FBN)

(b)

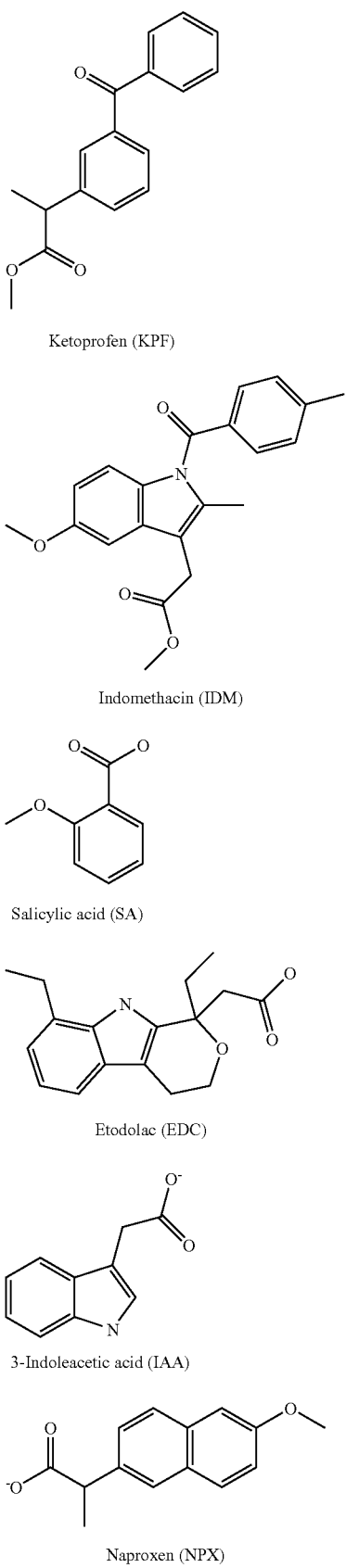

(c) Ketoprofen (KPF)

(d) Indomethacin (IDM)

(e) Salicylic acid (SA)

(f) Etodolac (EDC)

(g) 3-Indoleacetic acid (IAA)

(h) Naproxen (NPX)

Figure 2A:
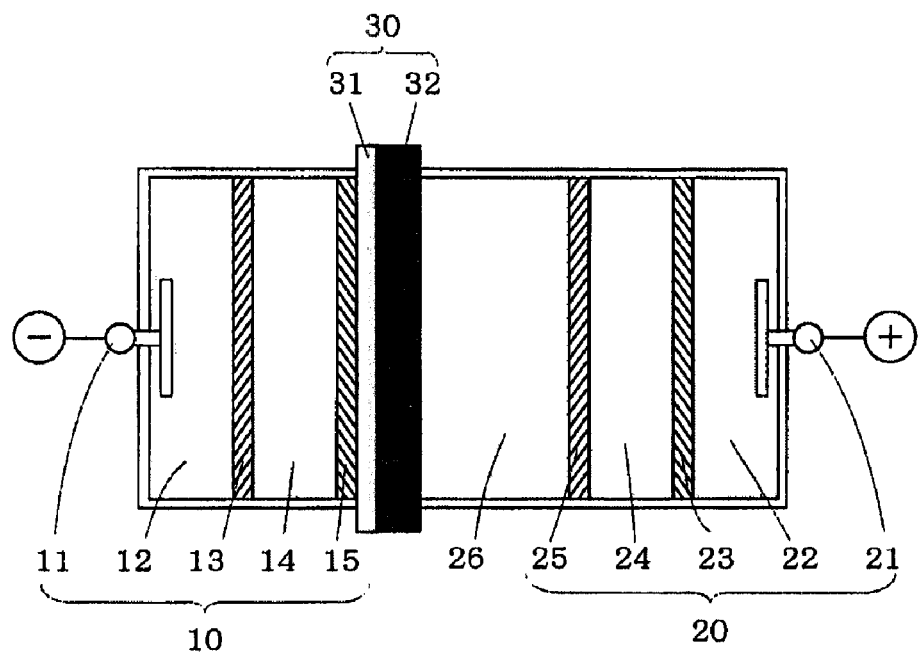
FIG. 2A is a schematic diagram of the experimental setup of FIG. 1 under a skin-present condition according to one illustrative embodiment.

Measurement 1: Measurement of Migration M of Drug Ion to Skin of Living Organism As shown in FIG. 2A, a corneal layer (surface skin) 31 of a skin 30 having a predetermined area harvested from the back of an SD-based rat was brought into contact with the anion exchange membrane 15 of the working side assembly 10. Energization was performed in a state where a corium layer 32 was brought into contact with the physiological salt solution of the electrolyte solution holding portion 26. After energization, the skin 30 was frozen and processed. Drug ions were extracted form the skin 30 with methanol, and the amount of the drug ion (unit: nmol/cm$^3$) that had migrated from the drug solution holding portion 14 to the skin 30 was measured by high performance liquid chromatography (HPLC). It should be noted that the drug solution concentration of each sample in the drug solution holding portion 14 was 6.25 mM, and the energization was performed at a constant current of 0.94 mA for 60 minutes.

The above measurement was performed 3 times for each sample, and the average value of the measurements was determined as the migration M.

Figure 2B:
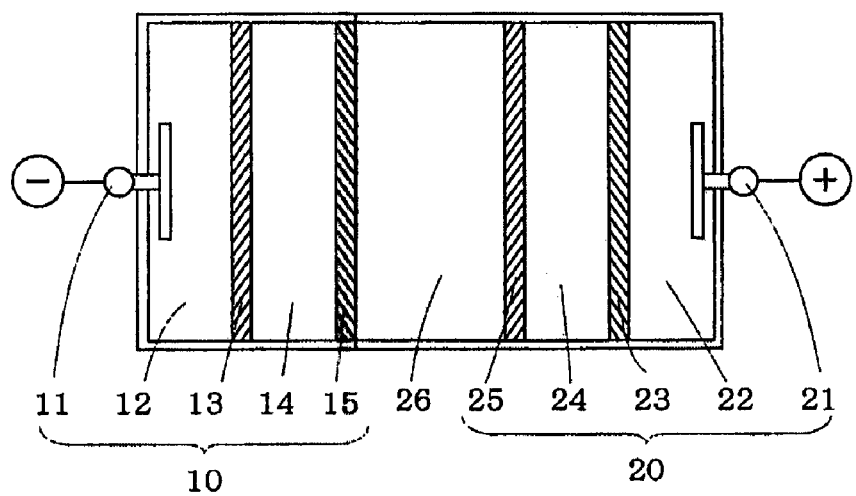
FIG. 2B is a schematic diagram of an experimental setup including a membrane type iontophoresis device used to obtain data associated with the migration C of the drug ion under a skin-absent condition according to one illustrative embodiment.
Figure 3A:
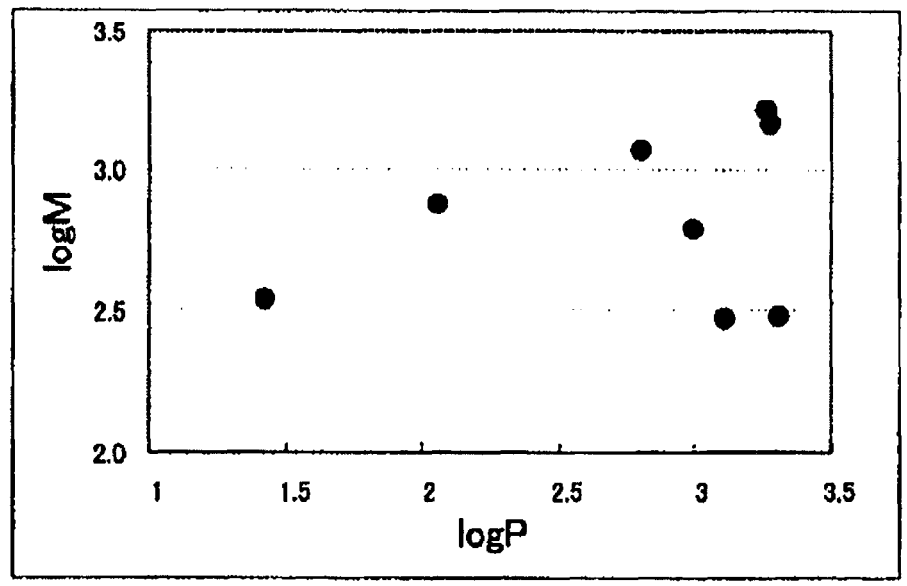
FIG. 3A is a graph of LogM versus LogP according to one illustrative embodiment.
Figure 3B:
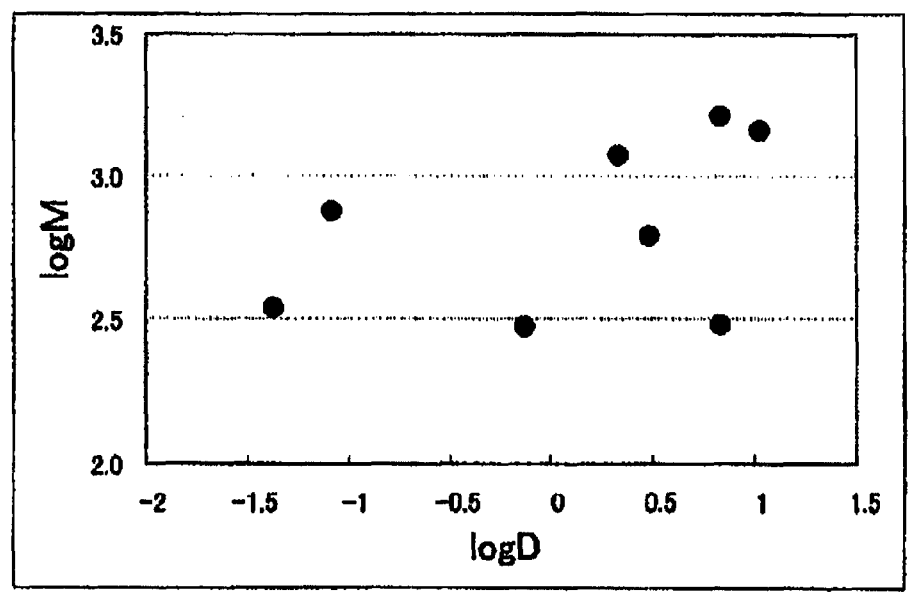
FIG. 3B is a graph of LogM versus LogD according to one illustrative embodiment.
Figure 3C:
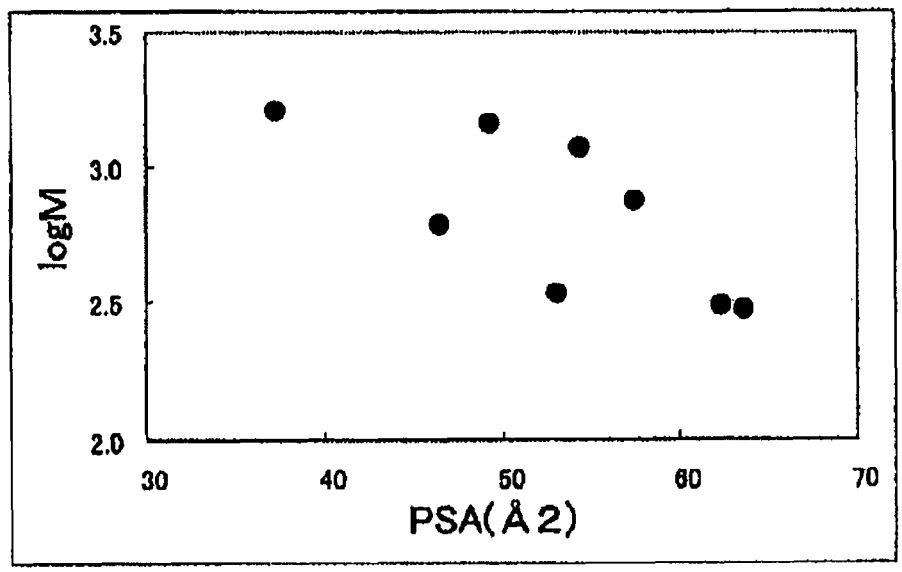
FIG. 3C is a graph of LogM versus PSA according to one illustrative embodiment.
Figure 3D:
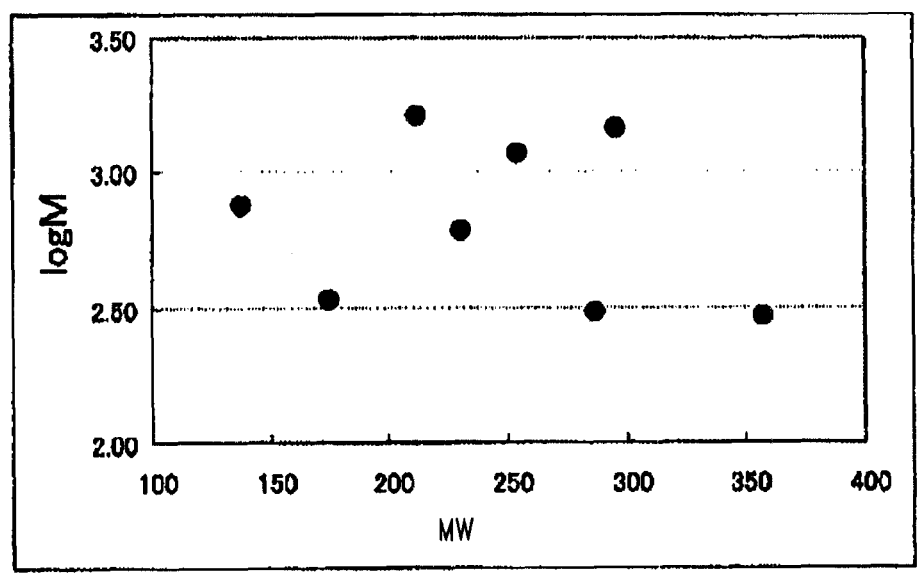
FIG. 3D is a graph of LogM versus Molecular Weight according to one illustrative embodiment.
Figure 3E:
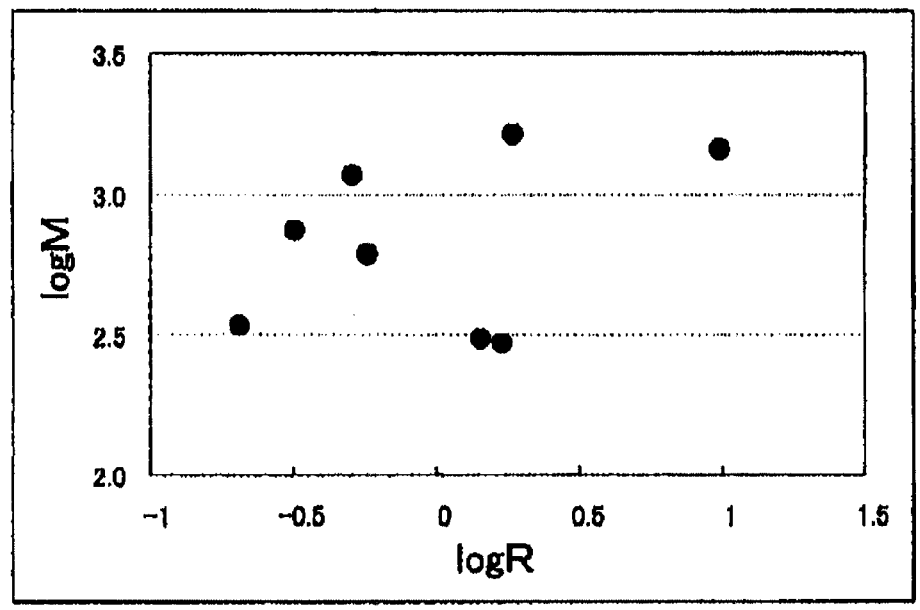
FIG. 3E is a graph of LogM versus LogR according to one illustrative embodiment.
Figure 3F:
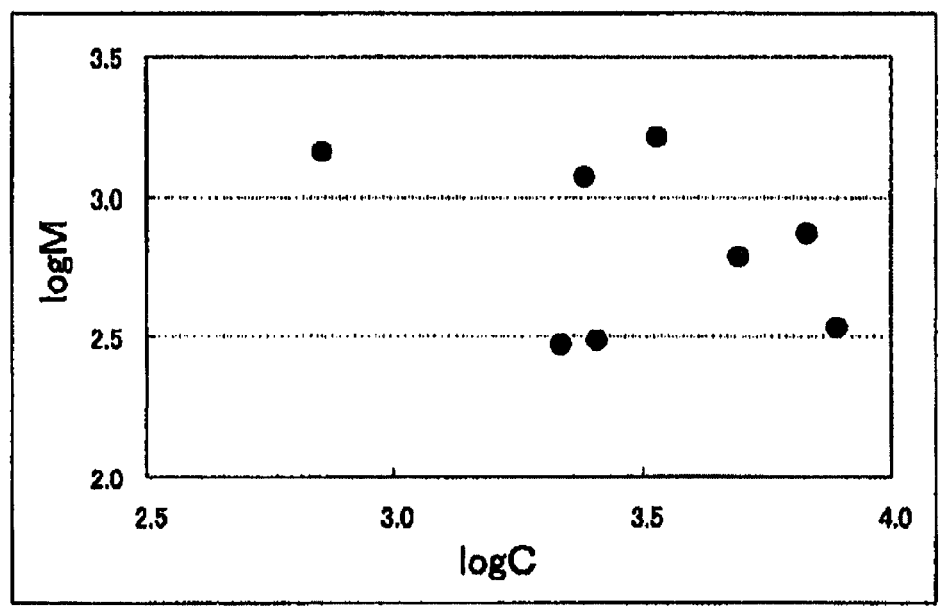
FIG. 3F is a graph of LogM versus LogC according to one illustrative embodiment.

Measurement 2: Measurement of Migration C of Drug Ion Under Skin-Absent Condition As shown in FIG. 2B, energization was performed in a state where the anion exchange membrane 15 of the working side assembly 10 was brought into contact with the physiological salt solution of the electrolyte solution holding portion 26, whereby the amount of the drug ion (unit: nmol/cm$^3$) that had migrated from the drug solution holding portion 14 to the electrolyte solution of the electrolyte solution holding portion 26 was measured. The drug solution composition of the drug solution holding portion 14, energization conditions, and the like were identical to those of Measurement 1.

The above measurement was performed 3 times for each sample, and the average value of the measurements was determined as the migration C.

Measurement 3: Measurement of Migration R of Drug Ion to Liposome 20 mM of an EPC liposome (yolk phosphatidylcholine (lecithin)/particle diameter 290 to 490 nm) and 3.125 mM of a drug solution were mixed at a volume ratio of 1:1, and the mixture was incubated at 37° C. for 18 hours. After that, the resultant was centrifuged, and the amount of a drug ion in each of the supernatant and the precipitate was measured by HPLC, whereby the amount of the drug ion (unit: nmol/cm$^3$) that had migrated to the EPC liposome was measured.

The above measurement was performed 3 times for each sample, and the average value of the measurements was determined as the migration R.

Table 1 summarizes the results of Measurements 1 to 3 described above. Table 1 shows LogP and LogD as hydrophobicity parameters, PSA as a parameter showing a hydrophilic region, and a molecular weight MW for each sample together with the results. It should be noted that values recorded in a database Scifinder provided by Japan Association for International Chemical Information were directly used as values for LogP, LogD, and PSA.

TABLE 1

Summary of Measured M, C, and R Values, as well as Predicted Log (M*/C) Values for Various Drugs.

| drug | Symbol | M | LogM | C | LogC | LogR | MW | LogP | LogD | PSA | Log(M/C) | Predicted Log(M*/C) |
|---|---|---|---|---|---|---|---|---|---|---|---|---|
| Indoleacetic acid | IAA | 341 | 2.53 | 7822 | 3.89 | −0.69 | 0.1752 | 1.43 | −1.37 | 53 | −1.36 | −1.2 |
| Salicylic acid | SA | 749 | 2.87 | 6800 | 3.83 | −0.49 | 0.1381 | 2.06 | −1.08 | 58 | −0.96 | −1.04 |
| Indomethacin | IDM | 296 | 2.47 | 2189 | 3.34 | 0.23 | 0.3578 | 3.11 | −0.13 | 64 | −0.87 | −0.49 |
| Ketoprofen | KPF | 1174 | 3.07 | 2432 | 3.39 | −0.29 | 0.2543 | 2.81 | 0.33 | 54 | −0.32 | −0.89 |
| Naproxen | NPX | 612 | 2.79 | 4940 | 3.69 | −0.24 | 0.2303 | 3 | 0.49 | 47 | −0.91 | −0.85 |
| Felbinac | FBN | 1622 | 3.21 | 3409 | 3.53 | 0.27 | 0.2122 | 3.26 | 0.83 | 37 | −0.32 | −0.45 |
| Diclofenac | DCF | 1445 | 3.16 | 718 | 2.86 | 0.99 | 0.2962 | 3.28 | 1.03 | 49 | 0.3 | 0.1 |
| Etodolac | EDC | 303 | 2.48 | 2576 | 3.41 | 0.16 | 0.2874 | 3.31 | 0.83 | 62 | −0.93 | −0.54 |
| Indolebutylic acid | IBA | 691 | 2.84 | 3744 | 3.58 | −0.26 | 0.2032 | 2.34 | −0.53 | 53 | −0.74 | −0.87 |
| Napthaleneacetic acid | NAA | 767 | 2.88 | 4806 | 3.68 | −0.47 | 0.1862 | 2.74 | −0.21 | 37 | −0.8 | −1.03 |

FIGS. 3A to 3F are each obtained by plotting LogP, LogD, PSA, MW, LogR, or LogC in Table 1. The axes of abscissa of FIGS. 3(A) to 3(F) indicate LogP, LogD, PSA, MW, LogR, and LogC, respectively, and the axis of ordinate of each of the figures indicates LogM.

As is apparent from the FIGS. 3A to 3F, a clear correlation between each of the factors (parameters) and the migration M is not observed. In has been found, however, that a generally linear correlation between LogR and LogM/C was valid as a result of the analysis of a relationship between each of various factors including those described above and the migration M by employing a correlation analysis method (Hansh-Fujita method).

Figure 4:
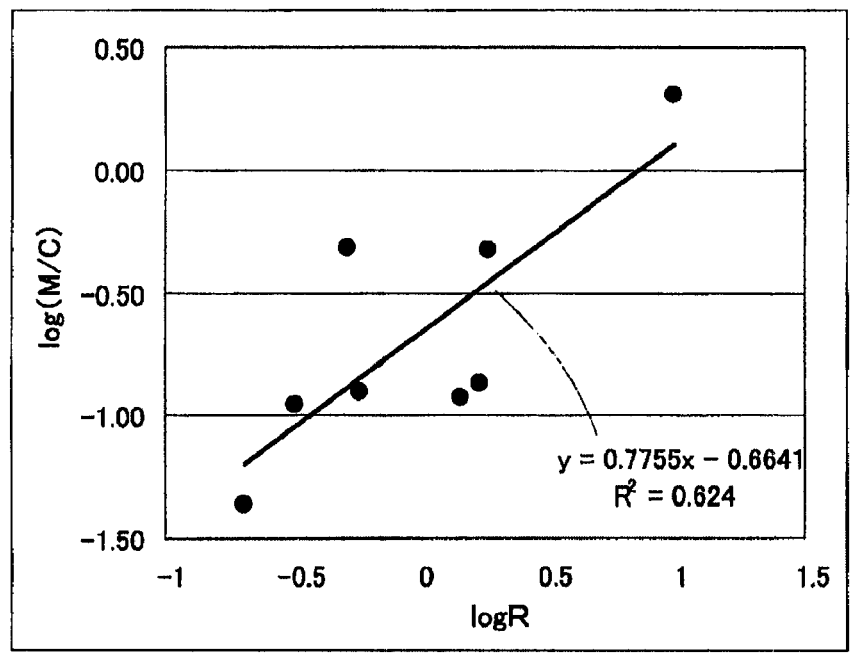
FIG. 4 is a graph of Log(M/C) versus Log R showing a correlation between Log(M/C) and LogR experimentally determined for each of various drug samples according to one illustrative embodiment.

FIG. 4 is obtained by plotting the results of Measurements 1 to 3 described above. The axis of abscissa of the figure indicates LogR, and the axis of ordinate of the figure indicates LogM/C.

As shown in FIG. 4, LogM/C determined by Measurements 1 to 3 for each of the above samples (a) to (h) is observed to show a strong correlation with LogR in accordance with the following Equation 2:

Log($M/C$)=0.7755×(Log $R$)−0.6641    (Eq. 2).

Therefore, the migration M of a drug ion to the skin 30, even when a novel drug that has never been administered with the iontophoresis device 1 and data on the migration M of which is unavailable is administered with the iontophoresis device 1, can be predicted using Equation 2 by measuring the migration C and migration R of the drug similarly to Measurements 2 and 3, and applying the measured values to the Equation 2.

Hereinafter, the results of an experiment for confirming the validity of the above Equation 2 are shown.

Novel drugs represented by the following formulae (i) and (j) (Indolebutyric acid: IBA, 1-Naphtaleneacetic acid: NAA) were used in the confirmation experiment.

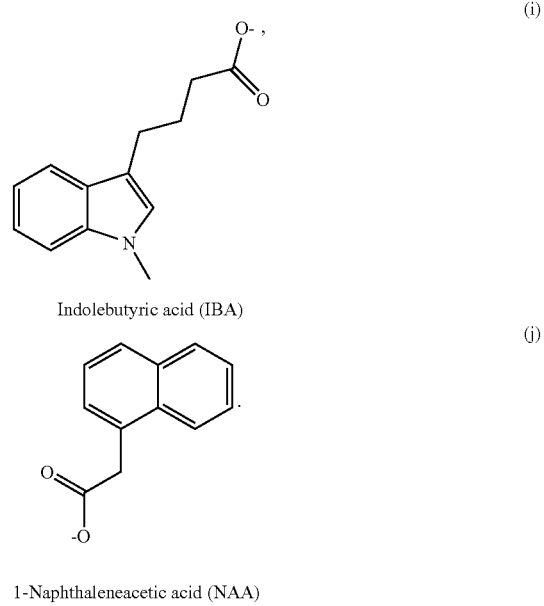

(i) Indolebutyric acid (IBA)

(j) 1-Naphthaleneacetic acid (NAA)

Figure 5:
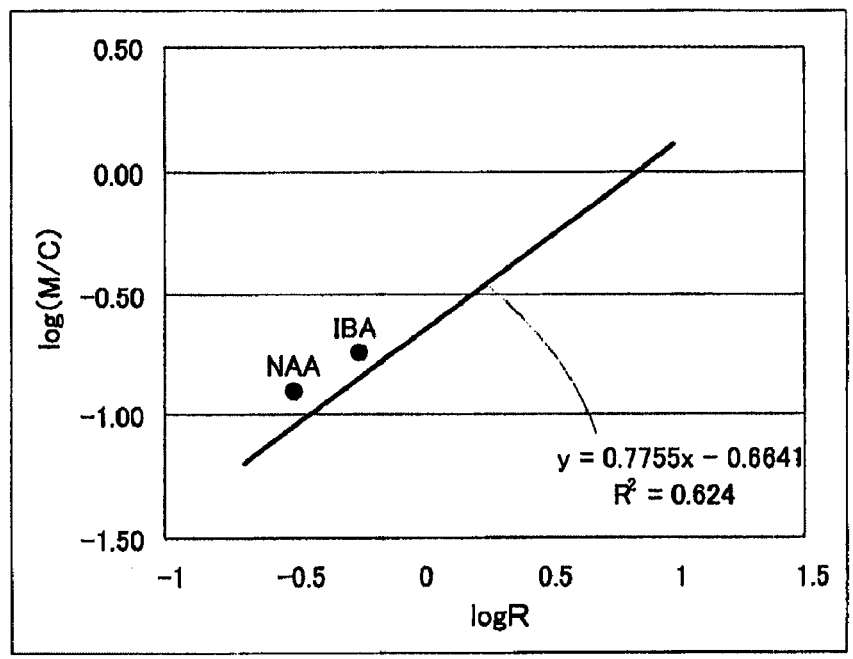
FIG. 5 is graph of Log(M/C) versus Log R showing the results of an experiment confirming an effect according to one illustrative embodiment.

Table 2 summarizes the results obtained by measuring the migration M, migration C, and migration R of each of both drugs similarly to Measurements 1 to 3. FIG. 5 is obtained by plotting the results in the same manner as in FIG. 4.

TABLE 2

Summary of Measured M, C, and R Values, as well as Predicted Log (M*/C) Values for Indolebutylic Acid and Napthaleneacetic Acid.

| drug | Symbol | M | LogM | C | LogC | LogR | MW | LogP | LogD | PSA | Log(M/C) | Predicted Log(M*/C) |
|---|---|---|---|---|---|---|---|---|---|---|---|---|
| Indolebutylic acid | IBA | 691 | 2.84 | 3774 | 3.58 | −0.26 | 0.2032 | 2.34 | −0.53 | 53.1 | −0.74 | −0.87 |
| Napthaleneacetic acid | NAA | 767 | 2.88 | 4806 | 3.68 | −0.47 | 0.1862 | 2.74 | −0.21 | 37.3 | −0.8 | −1.03 |

*M was determined as a function of measured C and R values.

As shown in FIG. 5, it was confirmed that the accurate prediction of the migration M of each of the above novel drugs (Indolebutyric acid: IBA, 1-Naphtaleneacetic acid: NAA) was attained by the Equation 2.

In the above embodiment, the above Equation 2 was determined by using the iontophoresis device 1 having the same components as that of the iontophoresis device 102 under specific conditions. When the migration M of a drug ion is predicted under conditions different from those described above (when, for example, the constitution of a membrane type iontophoresis device, a drug solution concentration, or an energization condition is different from that described above), coefficients $A_1$ and $A_2$ must be determined on the basis of values obtained by measuring the migration M, migration C, and migration R of each of several samples under the different conditions similarly to Measurements 1 to 3 described above.

In some embodiments, the coefficients $A_1$ and $A_2$ are determined under specific conditions, and the functional form of the above general Equation 1 is defined. After that, the function is can be implemented using, for example, a computing system. The migration M of a novel drug to the inside of the skin of a living organism under the specific conditions can be derived from measured values for the migration C and migration R of the novel drug.

In some embodiments, the present disclosure is directed to method of determining an amount of drug deliverable to a biological subject by an iontophoretic delivery device having a drug holding portion for holding a drug solution including drug ions of a first polarity, an electrode coupled to the drug holding portion and operable to apply an electrical potential of the first polarity to a drug solution held in the drug solution holding portion, and a first ion exchange membrane, having an exchange group of the first polarity, in contact with a front surface side of the drug solution holding portion.

The method includes determining a first drug migration parameter indicative of the migration of an amount of drug ions from the first ion exchange membrane to an outermost surface of the iontophoretic delivery device.

In some embodiments, determining the first drug migration parameter includes contacting a volume of physiological salt solution with the first ion exchange membrane, applying an electrical potential of the first polarity to the electrode for a time period, and measuring the amount of the drug ion that migrated from the drug solution holding portion to the volume of physiological salt solution.

In some embodiments, determining the first drug migration parameter includes contacting a volume of physiological salt solution with the iontophoretic delivery device including a 6.25 mM drug solution held in the drug holding portion, supplying a current of about 0.94 mA to the electrode for a period of about 60 minutes, and measuring the amount of the drug ion that migrated from the drug solution holding portion to the volume of physiological salt solution.

The method further includes determining a second drug migration parameter indicative of the migration of an amount of the drug ions migrated from a volume of a drug ion solution to a plurality of liposome in a volume of a liposome suspension after contacting the volume of the drug ion solution to the volume of the liposome suspension.

In some embodiments, determining the second drug migration parameter includes mixing a one-to-one by volume mixture of a suspension of egg phosphatidylcholine liposomes with a drug solution, incubating the mixture for a time period, and measuring the amount of the drug ion carrier by the egg phosphatidylcholine liposomes.

In some embodiments, determining the second drug migration parameter includes mixing a one-to-one by volume mixture of a suspension of liposomes with a drug solution, incubating the mixture for a time period, and measuring the amount of the drug ion carrier by the liposomes.

In some embodiments, determining the second drug migration parameter includes mixing a one-to-one by volume mixture of a 20 mM suspension of egg phosphatidylcholine liposomes with a 3 mM drug solution, incubating the mixture at about 37° C. for a time period of about 18 hours, and measuring the amount of the drug ion carrier by the egg phosphatidylcholine liposomes.

In some embodiments, determining the second drug migration parameter includes mixing in a one-to-one volume ratio of a 20 mM suspension of egg phosphatidylcholine liposomes having an average particle diameter ranging from about 290 nm to about 490 nm with a 3 mM drug solution, incubating the mixture at 37° C. for a time period of about 18 hours, and measuring the amount of the drug ion carrier by the egg phosphatidylcholine liposomes.

In some embodiments, the method may further include determining at least one of an iontophoretic drug ion delivery amount, iontophoretic drug ion delivery rate, an efficiency, and a dose based on the determined first drug migration parameter and the determining second drug migration parameter.

Figure 6:
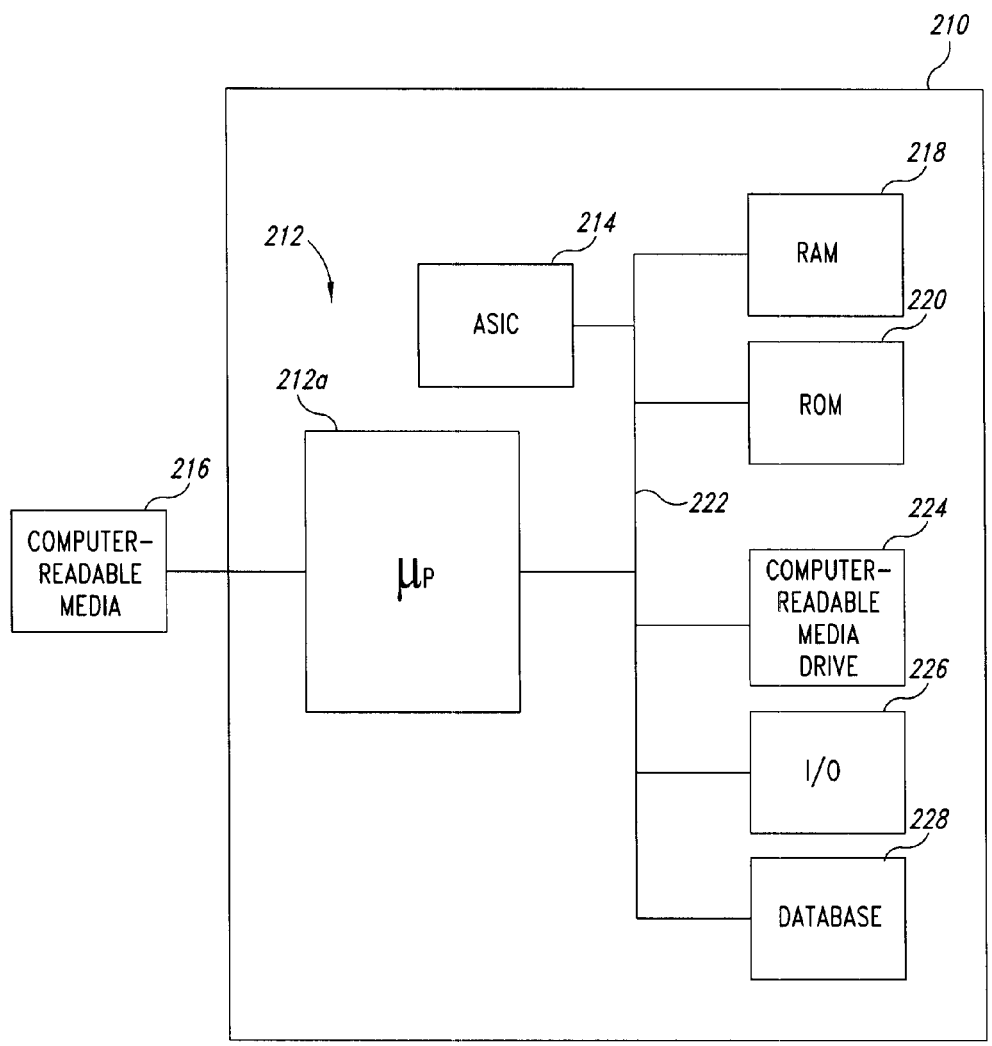
FIG. 6 is a schematic diagram of a computing system for executing one or more of the disclosed methods according to one illustrative embodiment.

FIG. 6 shows a block diagram of a computing system 210 suitable for executing any of the disclosed methods for determining an amount of drug deliverable to a biological subject by an iontophoretic delivery device, or the like. The computing system 10 may include one or more controllers 212 such as a microprocessor 12a, a central processing unit (CPU) (not shown), a digital signal processor (DSP) (not shown), an application-specific integrated circuit (ASIC) 14, a field programmable gate array, or the like, or combinations thereof, and may include discrete digital and/or analog circuit elements or electronics.

The computing system 210 may further include one or more memories that store instructions and/or data, for example, random access memory (RAM) 218, read-only memory (ROM) 220, or the like, coupled to the controller 212 by one or more instruction, data, and/or power buses 222. The computing system 210 may further include a computer-readable media drive or memory slot 224, and one or more input/output components 226 such as, for example, a graphical user interface, a display, a keyboard, a keypad, a trackball, a joystick, a touch-screen, a mouse, a switch, a dial, or the like, or any other peripheral device. The computing system 210 may further include one or more databases 228.

The computer-readable media drive or memory slot 224 may be configured to accept computer-readable memory media. In some embodiments, a program for causing the computer system 210 to execute any of the disclosed methods can be stored on a computer-readable recording medium. Examples of computer-readable memory media include CD-R, CD-ROM, DVD, data signal embodied in a carrier wave, flash memory, floppy disk, hard drive, magnetic tape, magnetooptic disk, MINIDISC, non-volatile memory card, EEPROM, optical disk, optical storage, RAM, ROM, system memory, web server, or the like.

In some embodiments, the computing system 210 is configured to determining the migration M of the drug ion to the inside of the skin of the living organism in the iontophoresis device based one the determined migration C and the determined migration R.

In some embodiments, the present disclosure is directed to at least one computer readable storage medium 216 comprising instructions that, when executed on the computing system 210, execute a method for determining an amount of drug deliverable to a biological subject by an iontophoretic delivery device having a drug holding portion for holding a drug solution including drug ions of a first polarity, an electrode coupled to the drug holding portion and operable to apply an electrical potential of the first polarity to a drug solution held in the drug solution holding portion, and a first ion exchange membrane, having an exchange group of the first polarity, in contact with a front surface side of the drug solution holding portion.

The method includes determining a first drug migration value indicative of the migration of an amount of drug ions from the first ion exchange membrane to an outermost surface of the iontophoretic delivery device. The method further includes determining a second drug migration value indicative of the migration of an amount of the drug ions migrated from a volume of a drug ion solution to a plurality of liposome in a volume of a liposome suspension after contacting the volume of the drug ion solution to the volume of the liposome suspension. The method further includes determining at least one of an iontophoretic drug ion delivery amount, iontophoretic drug ion delivery rate, an efficiency, and a dose based on the determined first drug migration value and the determining second drug migration value.

In some embodiments, the present disclosure is directed to computer system 10 including a memory and a processing unit 212 operable to execute a process of predicting a migration M of a drug ion having a first polarity to an inside of a skin of a living organism in an iontophoresis device having a drug solution holding portion for holding a drug solution containing the drug ion, a working side electrode for applying a voltage having the first polarity to the drug solution of the drug solution holding portion, and a first ion exchange membrane having the first polarity and placed in contact with the drug solution of the drug solution holding portion on a front surface side of the drug solution holding portion in a case where a voltage is applied to the working side electrode in a state where the first ion exchange membrane is brought into contact with the skin of the living organism, by: determining a migration C of the drug ion from the first ion exchange membrane to an outside of the iontophoresis device in a case where a voltage is applied to the working side electrode in the device under such a condition that the first ion exchange membrane is not brought into contact with the skin of the living organism; determining a migration R of the drug ion to a liposome in a case where a liposome solution having a predetermined concentration and the drug solution containing a predetermined concentration of the drug ion are mixed; and determining the migration M of the drug ion to the inside of the skin of the living organism in the iontophoresis device based one the determined migration C and the determined migration R.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to JP Appl. No. 2007-007328 filed Jan. 16, 2007, JP Pub. No. 04-297277 issued as JP Pat. No. 30-40517, and JP Pub. No. 2000-229128 are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of determining by a computer having at least one processor and at least one non-transitory processor-readable medium to store instructions executable by the at least one processor an amount of drug deliverable to a biological subject by an iontophoretic delivery device having a drug holding portion for holding a drug solution including drug ions of a first polarity, an electrode coupled to the drug holding portion and operable to apply an electrical potential of the first polarity to the drug solution held in the drug solution holding portion, and a first ion exchange membrane, having an exchange group of the first polarity, in contact with a front surface side of the drug solution holding portion, the method comprising:

determining a first drug migration parameter indicative of the migration of an amount of drug ions from the first ion exchange membrane to an outermost front surface side of the iontophoretic delivery device;

determining a second drug migration parameter indicative of the migration of an amount of the drug ions migrated from a volume of a drug ion solution to a plurality of liposomes in a volume of a liposome suspension after contacting the volume of the drug ion solution to the volume of the liposome suspension; and determining by the at least one processor at least one of an iontophoretic drug ion delivery amount, iontophoretic drug ion delivery rate, an efficiency, and a dose based on the determined first drug migration parameter and the determined second drug migration parameter;

wherein the values of the first and the second drug migration parameters are such as to yield a finite value for at least one of an iontophoretic drug ion delivery amount, an iontophoretic drug ion delivery rate, an efficiency, and a dose.

2. The method according to claim 1, wherein determining the first drug migration parameter includes contacting a volume of physiological salt solution with the first ion exchange membrane, applying an electrical potential of the first polarity to the electrode for a time period, and measuring the amount of the drug ion that migrates from the drug solution holding portion to the volume of physiological salt solution.

3. The method according to claim 1, wherein determining the first drug migration parameter includes contacting a volume of physiological salt solution with the iontophoretic delivery including a 6.25 mM drug solution held in the drug holding portion, supplying a current of about 0.94 mA to the electrode for a period of about 60 minutes, and measuring the amount of the drug ion that migrated from the drug solution holding portion to the volume of physiological salt solution.

4. The method according to claim 1, wherein determining the second drug migration parameter includes mixing a one-to-one by volume mixture of a suspension of egg phosphatidylcholine liposomes with a drug solution, incubating the mixture for a time period, and measuring the amount of the drug ion carrier by the egg phosphatidylcholine liposomes.

5. The method according to claim 1, wherein determining the second drug migration parameter includes mixing a one-to-one by volume mixture of a suspension of liposomes with a drug solution, incubating the mixture for a time period, and measuring the amount of the drug ion carried by the liposomes.

6. The method according to claim 1, wherein determining the second drug migration parameter includes mixing a one-to-one by volume mixture of a 20 mM suspension of egg phosphatidylcholine liposomes with a 3 mM drug solution, incubating the mixture at about 37° C. for a time period of about 18 hours, and measuring the amount of the drug ion carried by the egg phosphatidylcholine liposomes.

7. The method according to claim 1, wherein determining the second drug migration parameter includes mixing in a one-to-one volume ratio of a 20 mM suspension of egg phosphatidylcholine liposomes having an average particle diameter ranging from about 290 nm to about 490 nm with a 3 mM drug solution, incubating the mixture at 37° C. for a time period of about 18 hours, and measuring the amount of the drug ion carried by the egg phosphatidylcholine liposomes.

8. At least one computer readable storage medium comprising instructions that, when executed on a computer, execute a method for determining an amount of drug deliverable to a biological subject by an iontophoretic delivery device having a drug holding portion for holding a drug solution including drug ions of a first polarity, an electrode coupled to the drug holding portion and operable to apply an electrical potential of the first polarity to the drug solution held in the drug solution holding portion, and a first ion exchange membrane, having an exchange group of the first polarity, in contact with a front surface side of the drug solution holding portion, the method comprising:
 determining a first drug migration value indicative of the migration of an amount of drug ions from the first ion exchange membrane to an outermost surface side of the iontophoretic delivery device;
 determining a second drug migration value indicative of the migration of an amount of the drug ions migrated from a volume of the drug ion solution to a plurality of liposomes in a volume of a liposome suspension after contacting the volume of the drug ion solution to the volume of the liposome suspension; and
 determining at least one of an iontophoretic drug ion delivery amount, iontophoretic drug ion delivery rate, an efficiency, and a dose based on the determined first drug migration value and the determined second drug migration value;
 wherein the values of the first and second drug migration parameters are such as to yield a finite value for the at least one of an iontophoretic drug ion delivery amount, an iontophoretic drug ion delivery rate, an efficiency, and a dose.

9. A method of predicting by a computer having at least one processor and at least one non-transitory processor-readable medium to store instructions executable by the at least one processor a migration M of a drug ion having a first polarity to an inside of a skin of a living organism via iontophoresis using an iontophoresis device having a drug solution holding portion for holding a drug solution containing the drug ion, a working side electrode for applying a voltage having the first polarity to the drug solution of the drug solution holding portion, and a first ion exchange membrane having the first polarity and placed in contact with the drug solution of the drug solution holding portion on a front surface side of the drug solution holding portion, the method comprising:
 determining a migration C of the drug ion from the first ion exchange membrane to an outside of the iontophoresis device in a case where a voltage is applied to the working side electrode in the device under such a condition that the first ion exchange membrane is not brought into contact with the skin of the living organism;
 determining a migration R of the drug ion to a liposome in a case where a liposome solution having a predetermined concentration and the drug solution containing a
 deriving by the at least one processor a migration M of the drug ion to the inside of the skin of the living organism based on the determined migration C and migration R;
 wherein the values of the migration C and migration R are such as to yield a finite value for the migration M.

10. The method according to claim 9 wherein determining the migration C includes contacting the first ion exchange membrane to a volume of physiological salt solution, applying a voltage to the working side electrode of the iontophoresis device, and measuring the amount of the drug ion that migrated from the first ion exchange membrane to the volume of physiological salt solution.

11. The method according to claim 9 wherein determining the migration R includes contacting a liposome solution having the predetermined liposome concentration to the drug solution containing the predetermined concentration of the drug ion and measuring the amount of the drug ion that migrated from the drug solution containing the predetermined concentration of the drug ion to liposomes in the liposome solution having the predetermined liposome concentration.

12. The method according to claim 9 wherein deriving the migration M of the drug ion to the inside of the skin of the living organism based on the determined migration C and migration R includes deriving the migration M of the drug ion on the basis of the following formula (1):

$$\mathrm{Log}(M/C) = A_1 \mathrm{Log} R + A_2 \quad (1)$$

where C represents the migration of the drug ion from the first ion exchange membrane to the outside of the iontophoresis device in the case where a voltage is applied to the working side electrode in the iontophoresis device under such a condition that the first ion exchange membrane is not brought into contact with the skin of the living organism, R represents the migration of the drug ion to the liposome in the case where the liposome solution having the predetermined concentration and the drug solution containing the predetermined concentration of the drug ion are mixed, $A_1$ and $A_2$ each represent a constant, and C, R and M/C are non-zero, finite values.

13. The method according to claim 9 wherein the iontophoresis device further includes:
 a second ion exchange membrane having second polarity, the second ion exchange membrane being placed between the working side electrode and the drug solution holding portion; and
 an electrolyte solution holding portion for holding an electrolyte solution, the electrolyte solution holding portion being placed between the working side electrode and the second ion exchange membrane.

14. A computer system, comprising:
 a memory; and a processing unit operable to execute a process of predicting a migration M of a drug ion having a first polarity to an inside of a skin of a living organism in an iontophoresis device having a drug solution holding portion for holding a drug solution containing the drug ion, a working side electrode for applying a voltage having the first polarity to the drug solution of the drug solution holding portion, and a first ion exchange membrane having the first polarity and placed in contact with the drug solution of the drug solution holding portion on a front surface side of the drug solution holding portion in a case where a voltage is applied to the working side electrode in a state where the first ion exchange membrane is brought into contact with the skin of the living organism, by:

determining a migration C of the drug ion from the first ion exchange membrane to an outside of the iontophoresis device in a case where a voltage is applied to the working side electrode in the device under such a condition that the first ion exchange membrane is not brought into contact with the skin of the living organism;

determining a migration R of the drug ion to a liposome in a case where a liposome solution having a predetermined concentration and the drug solution containing a predetermined concentration of the drug ion are mixed; and determining the migration M of the drug ion to the inside of the skin of the living organism in the iontophoresis device based on the determined migration C and the determined migration R;

wherein the values of the migration C and the migration R are such as to yield a finite value for the migration M.

* * * * *

UNITED STATES PATENT AND TRADEMARK OFFICE
CERTIFICATE OF CORRECTION

| | | |
|---|---|---|
| PATENT NO. | : 7,925,520 B2 | Page 1 of 1 |
| APPLICATION NO. | : 12/015449 | |
| DATED | : April 12, 2011 | |
| INVENTOR(S) | : Kentaro Kogure et al. | |

It is certified that error appears in the above-identified patent and that said Letters Patent is hereby corrected as shown below:

Column 20, Lines 3-4:
"concentration and the drug solution containing a deriving by the at least one processor a migration M of the" should read, --concentration and the drug solution containing a predetermined concentration of the drug ion are mixed; and deriving by the at least one processor a migration M of the--.

Column 20, Line 43:
"of the drug ion are mixed, $A_1$ and $A_2$ each represent" should read, --of the drug ion are mixed, $A_1$ and $A_2$ each represent--.

Signed and Sealed this
Twenty-fifth Day of October, 2011

David J. Kappos
*Director of the United States Patent and Trademark Office*